(12) United States Patent
Ray et al.

(10) Patent No.: US 9,000,933 B2
(45) Date of Patent: Apr. 7, 2015

(54) AUTOMATED ALLERGY ALERTS

(75) Inventors: Sankar Ray, Sammamish, WA (US); Farooq Bari, Bothell, WA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 689 days.

(21) Appl. No.: 13/106,500

(22) Filed: May 12, 2011

(65) Prior Publication Data

US 2012/0286959 A1 Nov. 15, 2012

(51) Int. Cl.
| | | |
|---|---|---|
| G01N 21/53 | (2006.01) | |
| G06Q 50/24 | (2012.01) | |
| G08B 21/04 | (2006.01) | |
| G08B 21/12 | (2006.01) | |
| A61B 5/00 | (2006.01) | |

(52) U.S. Cl.
CPC .......... *G08B 21/043* (2013.01); *G08B 21/0461* (2013.01); *G08B 21/12* (2013.01); *A61B 5/6898* (2013.01); *A61B 5/411* (2013.01)

(58) Field of Classification Search
None
See application file for complete search history.

(56) References Cited

U.S. PATENT DOCUMENTS

| | | | |
|---|---|---|---|
| 6,288,646 B1* | 9/2001 | Skardon | 340/627 |
| 7,110,954 B2 | 9/2006 | Yung | |
| 7,787,887 B2 | 8/2010 | Gupta | |
| 7,876,214 B1 | 1/2011 | Brady, Jr. | |
| 2001/0029535 A1* | 10/2001 | Hirano et al. | 709/224 |
| 2002/0125313 A1* | 9/2002 | Broff | 235/383 |
| 2004/0006494 A1* | 1/2004 | Badinelli | 705/2 |
| 2004/0100380 A1* | 5/2004 | Lindsay et al. | 340/540 |
| 2004/0103043 A1* | 5/2004 | Reade et al. | 705/27 |
| 2005/0151656 A1* | 7/2005 | Yuen | 340/601 |
| 2007/0149212 A1 | 6/2007 | Gupta | |
| 2007/0298757 A1 | 12/2007 | Ahn | |
| 2008/0133336 A1 | 6/2008 | Altman | |
| 2010/0241350 A1 | 9/2010 | Cioffi | |
| 2010/0269058 A1 | 10/2010 | Othmer | |
| 2011/0045847 A1 | 2/2011 | Roin | |
| 2011/0054776 A1 | 3/2011 | Petrov | |
| 2011/0318717 A1* | 12/2011 | Adamowicz | 434/127 |

* cited by examiner

*Primary Examiner* — Brian Zimmerman
*Assistant Examiner* — Cal Eustaquio
(74) *Attorney, Agent, or Firm* — Guntin & Gust, PLC; Joseph P. Hrutka

(57) ABSTRACT

Devices, systems, and methods are disclosed which relate to utilizing a wireless communication device which receives allergy information from network nodes. The wireless communication device contains an allergy profile for the user. When the wireless communication device receives allergy information this allergy profile is referenced to determine if any allergens near the user may cause a problem for the user. If allergens exist to which the user is allergic, a visual, aural, and/or tactile alert is output on the wireless communication device.

20 Claims, 7 Drawing Sheets

AUTOMATED ALLERGY ALERTS

BACKGROUND OF THE SUBJECT DISCLOSURE

1. Field of the Subject Disclosure

The present subject disclosure relates to allergy information. More specifically, the present subject disclosure relates to automated allergy alerts.

2. Background of the Subject Disclosure

There have been many documented cases where significant health emergencies, including the loss of life, have resulted from inadvertent exposure to life threatening food allergens, such as peanuts, tree-nuts, egg yolk, shellfish, etc. There is an extremely serious, and potentially life-threatening, issue of inadvertent exposure to food-based allergens from prepared food sources accessible to the general public.

The only current mechanism to discover the presence of food allergens in prepared food is asking a food server interfacing with the customer. This mechanism frequently has zero, incorrect, or incomplete information on the individual ingredients that make up the prepared food being served. The problem becomes acute when language issues are involved.

At the same time, mobile devices, such as cellular telephones, have become a common tool of everyday life. Cellular telephones are no longer used simply to place telephone calls. With the number of available features rapidly increasing, cellular telephones are now used for storing addresses, keeping a calendar, reading e-mails, drafting documents, etc. These devices are small enough that they can be carried in a pocket or purse all day, allowing a user to stay in contact almost anywhere. Recent devices have become highly functional, providing applications useful to business professionals as well as the casual user. Many of these devices support multiple communication protocols in addition to those of cellular communication, including WiFi, BLUETOOTH, ZIGBEE, Z-WAVE, etc.

What is needed is a mobile phone based alerting solution to prevent inadvertent exposure to allergens from sources for such potential exposures, such as restaurants, cafeterias, food vending machines, factories, etc.

SUMMARY OF THE SUBJECT DISCLOSURE

The present subject disclosure solves the problems outlined above by utilizing a wireless communication device which receives allergy information from network nodes dedicated for this purpose or existing network entities, such as access points. In exemplary embodiments, a wireless communication device contains an allergy profile for the user. When the wireless communication device receives allergy information this allergy profile is referenced to determine if any allergens near the user may cause an adverse medical impact for the user. If allergens exist to which the user is allergic, a visual, aural, and/or tactile alert is output on the user's wireless communication device.

In one exemplary embodiment, the present subject disclosure is a wireless communication device. The device includes a processor, a memory in communication with the processor, a transceiver in communication with the processor, and an allergy alert logic on the memory which receives an allergy announcement from a network node, the announcement identifying an allergen present at a location, determines that a user is allergic to the allergen present at the location by referencing an allergy profile stored in the memory, and alerts the user of the location and the allergen.

In another exemplary embodiment, the present subject disclosure is a system for allergy alerts. The system includes a wireless communication device, a network node in communication with the wireless communication device, an allergen database in communication with the network node, the allergen database including allergens present at a location, an allergy alert logic on the wireless communication device which receives an allergy announcement from a network node, the announcement including allergens present at the location, determines that a user is allergic to at least one allergen present at the location, and alerts the user of the location and the allergen.

In yet another exemplary embodiment, the present subject disclosure is a method for alerting a user of a location having an allergen to which the user is allergic. The method includes receiving an allergy announcement from a network node, the announcement received on a wireless communication device, the announcement including allergens present at a location, determining that a user is allergic to at least one allergen present at the location, and alerting the user of the location and the allergen.

DETAILED DESCRIPTION OF THE SUBJECT DISCLOSURE

Figure 1A:
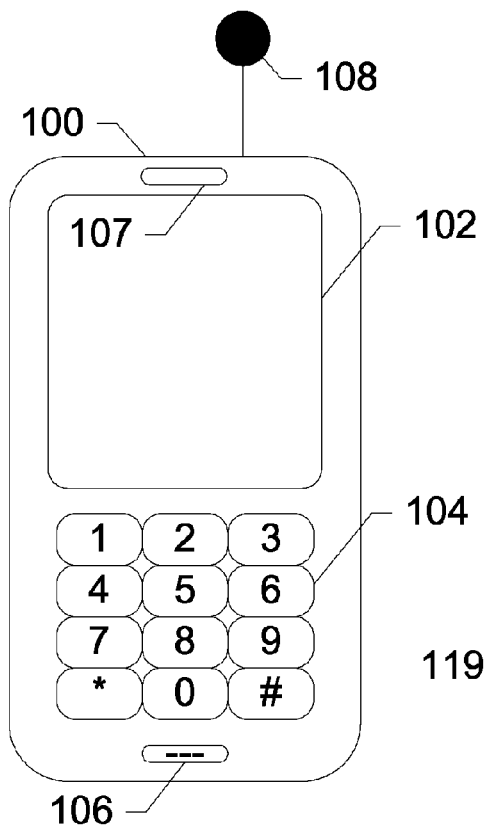
FIG. 1A shows a wireless communication device for automated allergy alerts, according to an exemplary embodiment of the present subject disclosure.

The present subject disclosure solves the problems outlined above by utilizing a wireless communication device which receives allergy information from network nodes dedicated for this purpose or existing network entities, such as access points. In exemplary embodiments, a wireless communication device contains an allergy profile for the user. When the wireless communication device receives allergy information this allergy profile is referenced to determine if any allergens near the user may cause an adverse medical impact for the user. If allergens exist to which the user is allergic, a visual, aural, and/or tactile alert is output on the user's wireless communication device.

"Wireless communication device", as used herein and throughout this disclosure, refers to any electronic device capable of wirelessly sending and receiving data. A wireless communication device may have a processor, a memory, a transceiver, an input, and an output. Examples of such devices include cellular telephones, personal digital assistants (PDAs), portable computers, etc. The memory stores applications, software, or logic. Examples of processors are computer processors (processing units), microprocessors, digital signal processors, controllers and microcontrollers, etc. Examples of device memories that may comprise logic include RAM (random access memory), flash memories, ROMS (read-only memories), EPROMS (erasable programmable read-only memories), and EEPROMS (electrically erasable programmable read-only memories).

"Logic", as used herein and throughout this disclosure, refers to any information having the form of instruction signals and/or data that may be applied to direct the operation of a processor. Logic may be formed from signals stored in a device memory. Software is one example of such logic. Logic may also be comprised by digital and/or analog hardware circuits, for example, hardware circuits comprising logical AND, OR, XOR, NAND, NOR, and other logical operations. Logic may be formed from combinations of software and hardware. On a telecommunication network, logic may be programmed on a server, or a complex of servers. A particular logic unit is not limited to a single logical location on the telecommunication network.

Wireless communication devices communicate with each other and with other elements via a network, for instance, a wireless network, or a wireline network. A "network" can include broadband wide-area networks such as cellular networks, local-area networks (LAN), and personal area networks, such as near-field communication (NFC) networks including BLUETOOTH®. Wireless communication devices communicate with a network through a "network node". Examples of network nodes include wireless routers, cellular base stations, etc. Communication across a network is preferably packet-based; however, radio and frequency/amplitude modulations networks can enable communication between wireless communication devices using appropriate analog-digital-analog converters and other elements. Communication is enabled by hardware elements called "transceivers." Wireless communication devices may have more than one transceiver, capable of communicating over different networks. For example, a cellular telephone can include a cellular transceiver for communicating with a cellular base station, a Wi-Fi transceiver for communicating with a Wi-Fi network, and a BLUETOOTH® transceiver for communicating with a BLUETOOTH® device. A network typically includes a plurality of elements that host logic for performing a variety of tasks on the network.

For the following description, it can be assumed that most correspondingly labeled structures across the figures (e.g., 113 and 213, etc.) possess the same characteristics and are subject to the same structure and function. If there is a difference between correspondingly labeled elements that is not pointed out, and this difference results in a non-corresponding structure or function of an element for a particular embodiment, then that conflicting description given for that particular embodiment shall govern.

FIG. 1A shows a wireless communication device 100 for automated allergy alerts, according to an exemplary embodiment of the present subject disclosure. In this exemplary embodiment, wireless communication device 100 includes a display 102, a keypad 104, a microphone 106, a speaker 107, and an antenna 108. Display 102 is a liquid crystal display (LCD) that serves as a visual output for the user. Display 102 is used to display, among other things, allergy alerts and setup screens for allergy alerts and profile editing. Keypad 104 is an input for entering information and commands to wireless communication device 100. Microphone 106 accepts aural input and allows wireless communication device 100 to deliver voice communication to the network and other wireless communication devices. Speaker 107 outputs audio, such as for aural allergy alerts, and also allows voice communication with other wireless communication devices. Antenna 108 sends and receives wireless radio frequency (RF) signals to and from wireless networks, network nodes, and other wireless devices.

Figure 1B:
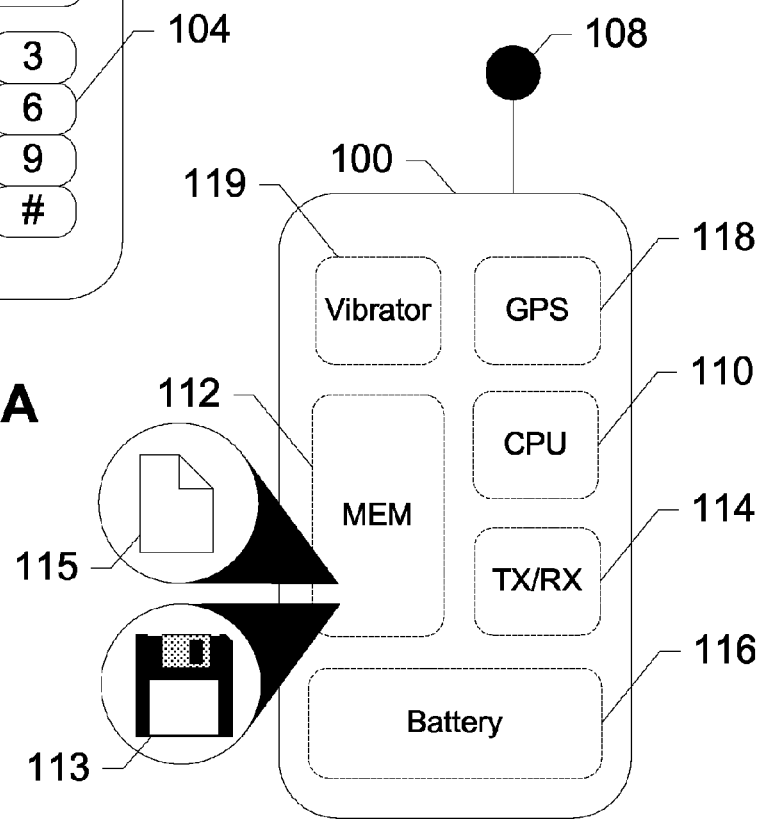
FIG. 1B shows the interior components of a wireless communication device for automated allergy alerts, according to an exemplary embodiment of the present subject disclosure.

FIG. 1B shows the interior components of a wireless communication device 100 for automated allergy alerts, according to an exemplary embodiment of the present subject disclosure. The inner components of wireless communication device 100 include a processor 110, a memory 112 storing an allergy alert logic 113 and the user's allergy profile data 115, a transceiver 114, a battery 116, a global positioning system (GPS) 118, and a vibrator 119. Processor 110 receives input and issues commands to deliver output through the other components. Memory 112 stores information including logic for enabling processor 110 to operate the other components of wireless communication device 100, and further stores allergy alert logic 113. Allergy alert logic 113 receives allergy announcements from network nodes and alerts the user when an allergen is near. Allergy alert logic 113 maintains the user's allergy profile data 115 and alerts settings. Transceiver 114 converts wireless signals received by antenna 108 to information capable of processing by processor 110, and vice-versa, and to communicate with the cellular network and other wireless communication devices. Transceiver 114 uses one or more short-range wireless protocols, including WiFi, BLUETOOTH, ZIGBEE, Z-WAVE, etc., to communicate with network nodes and other wireless communication devices within range. Battery 116 powers wireless communication device 100, and may be rechargeable via an external power source. GPS 118 communicates with satellites to determine the location of wireless communication device 100 within a few meters. Allergy alert logic 113 may reference GPS 118 when determining whether the user is close enough to an allergen to make an alert. Vibrator 119 is included to assist wireless communication device 100 in alerting the user when an allergen is nearby.

There are many embodiments of a wireless communication device that are capable of being used in accordance with the present subject disclosure. For instance, many legacy model cellular telephones are capable of executing the allergy alert logic described above. In other embodiments of the wireless communication device, other displays are used, such as an LED display, OLED display, etc. In some embodiments, the display is used as a touch-sensitive input device, i.e. a touch screen. A touch screen allows the user to view output on the display as well as use the display to provide input. In some touch screen embodiments the mobile device may not have a physical keypad for input. Instead, a virtual keypad is displayed on the touch screen and the user inputs by touching the virtual keys. Other forms of input such as full keyboards, accelerometers, motion sensors, etc., can be utilized in the wireless communication device. The memory can be a non-removable internal memory, or a removable memory such as in a subscriber identity module (SIM) card or a memory card inserted into a memory card reader. Many mobile devices have more than one transceiver or a transceiver that supports more than one protocol. For instance, it is not uncommon for a mobile device to support cellular radio frequency (RF), NFC, WiFi, BLUETOOTH®, ZIGBEE®, and Z-WAVE® protocols. A wireless communication device involving multiple modes of wireless communications, such as cellular, WiFi, NFC, etc., may contain a plurality of antennas on a single device. For example, an NFC-enabled wireless communication device has separate antennas for cellular and NFC communications respectively.

In this exemplary embodiment, the wireless communication device has a resident application on the memory, the allergy alert logic, which is designed to operate over one or more short-range wireless connectivity technologies, such as WiFi, BLUETOOTH, ZIGBEE, Z-WAVE, etc. The allergy alert logic is preconfigured to maintain and access a stored allergy profile data containing specific allergies of the wireless communication device user. It is also configured to search for and listen to a network node that broadcasts an updated list of common food allergens currently present at the location as soon as it detects the presence of a compatible wireless connectivity technology. It is also configured to retrieve the current location of the device from the device-resident GPS function.

There are two different implementations of the allergy alerting system: wide-area and local. For a wide-area implementation using a central allergy server, the user selects a location, such as restaurant, an intersection, a GPS coordinate set, and queries the central server's stored database for an allergy announcement pertinent to the selected location. This is a query-response based implementation, not a broadcast. For a local implementation the user's wireless communication device picks up a broadcast of an allergy announcement, from network nodes of restaurants, shops, etc., as it approaches the vicinity of the selected location. In this implementation the user's wireless communication device does not actively query for allergen info, but is simply set on 'listen' mode.

Figure 2:
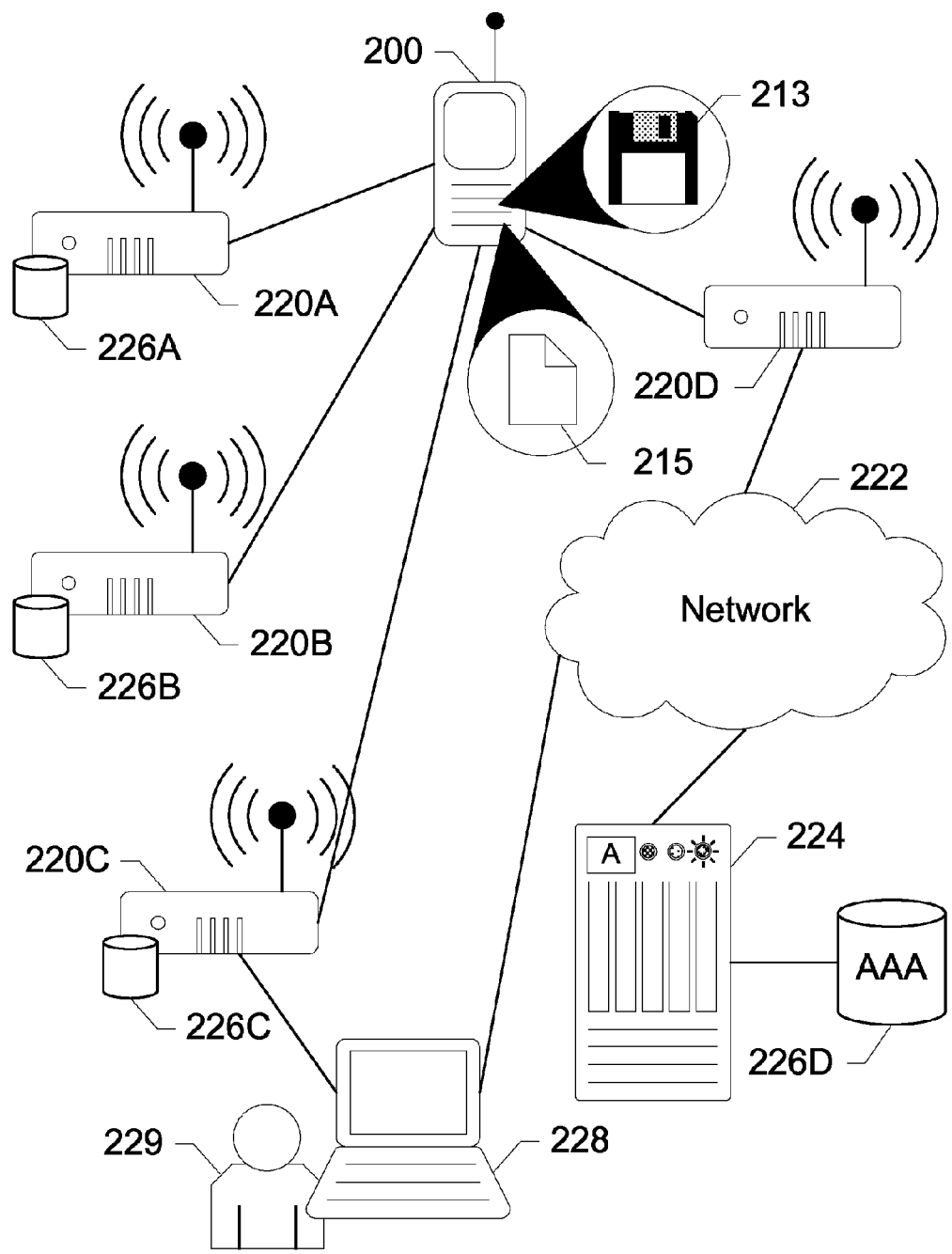
FIG. 2 shows a system for automated allergy alerts, according to an exemplary embodiment of the present subject disclosure.

FIG. 2 shows a system for automated allergy alerts, according to an exemplary embodiment of the present subject disclosure. In this exemplary embodiment, the system includes a personal wireless communication device 200 including an allergy alert logic 213 containing the allergy profile data 215, network nodes 220A-D, allergen databases 226A-D, a network 222, an allergy server 224, an update computer 228, and a manager 229. Wireless communication device 200 receives allergy announcements from network nodes 220A-C. Network nodes 220A-C each broadcast an allergy announcement on a periodic basis. Each network node 220A-C represents a location where allergies may exist, such as restaurants, stores, factories, vending machines, etc. Each database 226A-C includes a list of allergens currently at the corresponding location. For example, any given network node and associated database may be based in a regional medical facility/service. The area covered by any given network node and associated database may include many commercial and/or public enterprises participating in a central allergy alerting system. When wireless communication device 200 receives an allergy announcement from a network node, allergy alert logic 213 compares the allergens in the allergy announcement with the user's stored allergy profile 215 to determine if the user is allergic to any of the allergens present at the location.

This allergy profile may be stored on wireless communication device 200 or elsewhere within the system, such as a centrally located allergy server 224. Wireless communication device 200 also communicates with network node 220D, which accesses a wide-area network 222, for example a cellular or WiMax network, and ultimately allergy server 224. Allergy server 224 receives allergen updates for a plurality of locations within its designated coverage area. Rather than broadcast every allergen at every location, allergy server 224 responds to requests for allergy information. Wireless communication device 200 sends a request for allergy information along with a specific location(s). Allergy server 224 references allergen database 226D for the most up to date allergens information for the specific location(s) within the area served by 224. Allergy server 224 then sends an allergy announcement for each queried location to the wireless communication device 200. Manager 229 updates allergen databases 226C and 226D from update computer 228 whenever information about a new allergen within the area covered by network node 226C is made available to the manager. The updating of allergen databases 226C and 226D by Manager 229 assumes a pre-established trust relationship, and data connectivity, between the participating enterprises and Manager 229.

Allergen databases 226A, B, and C, representing an individual location, such as a restaurant) can be updated over the local area network at the location of manager 229. Updating central allergen database 226D is also possible requiring connection to network 222, which manager 229 can do through a wireless connection from update computer 228 to network 222.

Exemplary embodiments of a local server-based application, which is part of the vendor's data infrastructure, broadcasts, through the network node, a well-known code that identifies itself as the authoritative source for the list of food allergens in the immediate vicinity. This allergy announcement also includes a list of pre-established codes correlated with specific allergens that can be decoded by the allergy alert logic on the wireless communication device. The allergy alert logic receives the announcement, decodes the list of allergens present, correlates it with the specific allergen/s in its own stored database as configured by the user and/or by authorized medical professional and sets off an audible/visible alert if there is a match, as described above.

In some embodiments, manager 229 only updates one of the local and central databases. In other embodiments the allergy server is periodically updated with the location of the wireless communication device utilizing device-resident GPS information and sends an allergy announcement to the wireless device using a "push" mechanism anytime a match is found between the specific location, the location of an allergen, and a pre-established allergy profile stored in the wireless communication device.

Allergen databases are updated by local managers or other personnel at the location who have first-hand knowledge of the allergen contents at the location. In some embodiments, the ability to add allergens can be granted liberally while the ability to remove allergens can be safeguarded. In this respect, anyone who notices an allergen missing from the list can add the allergen before a problem arises. These embodiments are set to err on the side of caution with too many allergens. While business may curtail from false positives, problems are more likely avoided. When updating the allergen database on the network, the application server may require the manager to provide security credentials in order to modify the allergen contents at their location. The local manager sets the allergy announcement over WiFi at the start of the business day. A WiFi broadcast prefix indicates this is an allergy alert, authenticates the source as authoritative, and may add the name of the business.

Exemplary embodiments of the present subject disclosure describe alerting mechanisms, both automated and non-automated, that make use of the user's wireless communication device in cooperation with corresponding supporting capabilities added to the communication infrastructure of a food provider, store owner, factory foreman, vending machine operator, etc. Exemplary embodiments of the present subject disclosure work over any short-range wireless communication technology (WiFi, BLUETOOTH, ZIGBEE, Z-WAVE, etc.), Near Field Communication (NFC) technology for the 'local' implementation, and any cellular (3G, 4G, WiMax, LTE, etc.) or wide-area communication technology depending on the preferences of vendors and users as well as the circumstances of use for a 'wide area' implementation. All exemplary embodiments of the present subject disclosure, reliant on a broadcast mechanism, shall not compromise the user's privacy. The vendor-based network node remains unaware of customer-specific medical information. Furthermore, query-based embodiments only require disclosure of the user's location. A central allergy server responds to such a query with an allergy announcement containing information about all of the allergens in or nearby the user's location. The user's wireless communication device then compares the allergy announcement with the allergy profile to determine whether or not to alert the user.

In some embodiments of the present subject disclosure the user's wireless communication device checks for the presence of allergens in the immediate vicinity of the user. The source of allergens (such as restaurants, cafeterias, factories, vending machines, etc.) must participate in facilitating and updating the data used in the alerts. Exemplary embodiments of the determination of allergens and allergy alerts are automated. Network nodes of local area networks may be used by vendors for allergy announcements stemming from the location of the allergens in some embodiments. For embodiments where the local broadcast mechanism is not available, possible, or desired at the allergy location, allergy information can be uploaded from the vendor into a central database on a wide-area network, such as a cellular network. This central database is accessed through the network node of the wide-area network by the wireless communication device when allergy information is desired or required.

Figure 3:
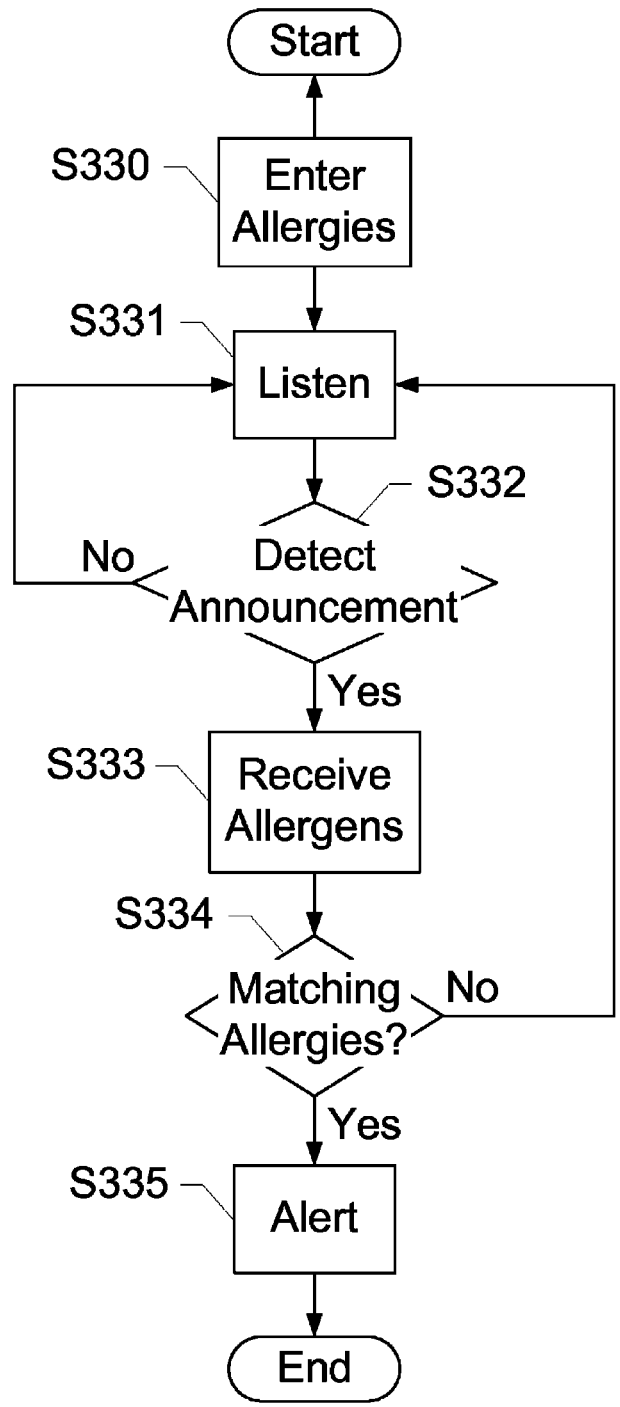
FIG. 3 shows a method of automating allergy alerts, according to an exemplary embodiment of the present subject disclosure.

In many embodiments, NFC technology is used for vending machines and other similar venues to prevent allergens exposure to the user. In these embodiments using NFC, the allergen contents of the offered food items of the vending machine are contained in an NFC tag attached to the vending machine. The user actively checks for alerts by touching or holding the wireless communication device near a designated spot and reads the content of the NFC tags. network node FIG. 3 shows a method of automating allergy alerts in the form of a flowchart, according to an exemplary embodiment of the present subject disclosure. This exemplary embodiment begins when a user, or authorized medical personnel, enters their allergies into a profile, such as on a wireless communication device S330. Once the allergies have been entered into the profile, the wireless communication device is placed in a passive listening mode S331, where it listens for allergy announcements S332. When an allergy announcement is received, the wireless communication device reads allergen codes from the announcement S333. Next, the profile is referenced to determine if the allergen codes from the allergy announcement match with any of the allergies entered into the profile S334. If no matches are found, then the wireless communication device returns to the passive listening mode. If a match is found, then the wireless communication device alerts the user of the presence of allergens S335. The alert can be a visual, aural, tactile, or any combination.

Once the allergy alert logic is configured, the process is automated, requiring no user interaction. Also, there is no need, at the very simplest level of operation, for the allergy alert logic to actually establish a data connection with the network node since the allergy alert logic is simply in a "Listen" mode receiving allergy announcements. The "Listen" mode saves both battery power and ensures that no private user information is transmitted to a public entity.

There is, however, an implied requirement to agree on a set of pre-established codes that can be correlated with allergens to avoid text-based information. This solution lends itself more to a restaurant/cafeteria scenario where the type of food changes on a daily basis and resources are also available to update the allergy announcement on a daily basis. In other embodiments, the user may have a physician or other medical professional enter allergies for the user onto the wireless communication device. When the allergen codes are read from the allergy announcement, the wireless communication device may be set to store the allergen codes and the location for future reference. This is an option that can be set by the user, along with options to set an expiration of those allergen codes for that location.

Figure 4:
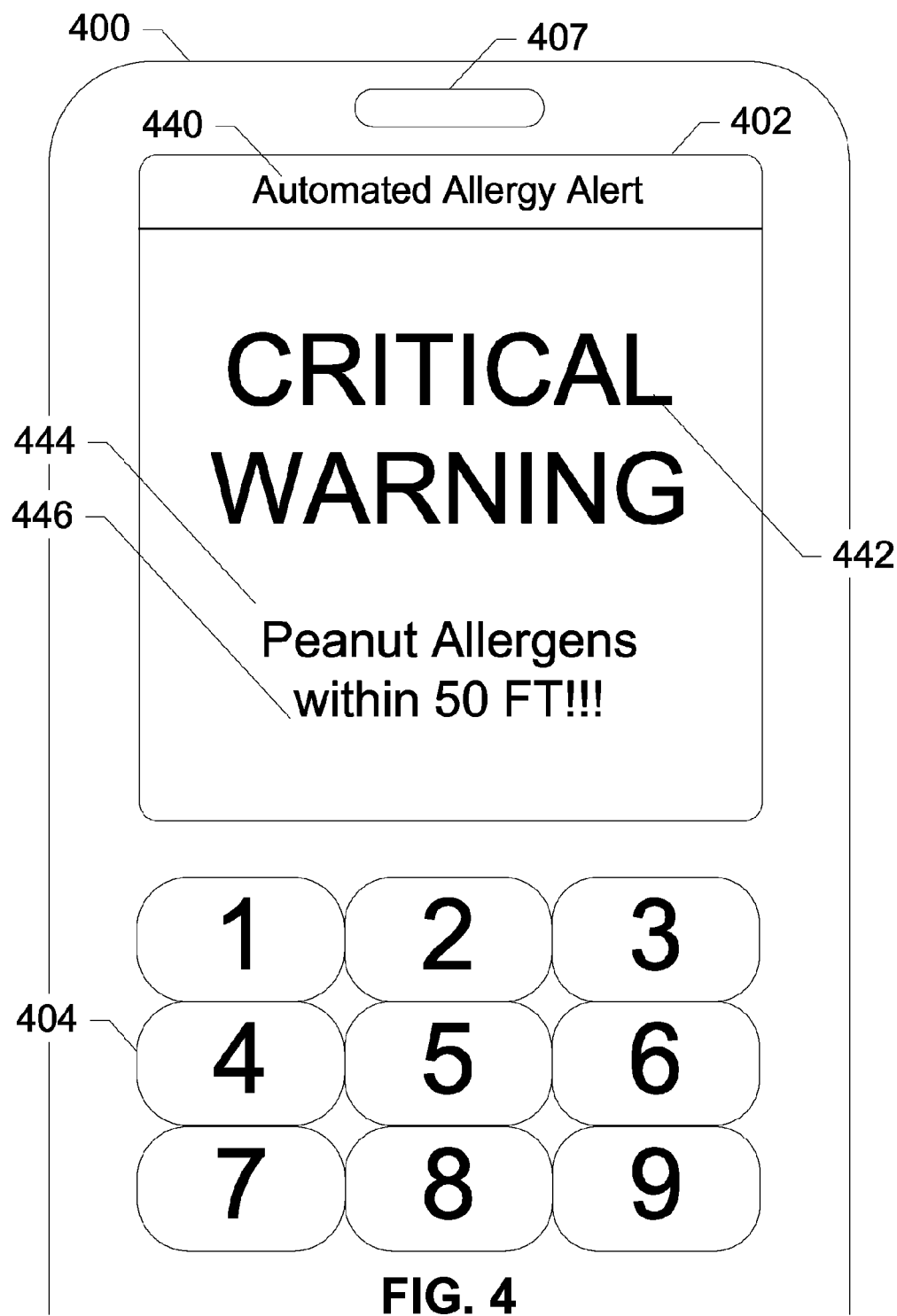
FIG. 4 shows an allergy alert on a wireless communication device, according to an exemplary embodiment of the present subject disclosure.

FIG. 4 shows an allergy alert 440 on a wireless communication device 400, according to an exemplary embodiment of the present subject disclosure. In this exemplary embodiment, wireless communication device 400 has received an allergy announcement from a network node, and has determined that at least one allergen code in the allergy announcement matches an allergen in the user's stored allergy profile. Therefore, wireless communication device 400 must issue an allergy alert 440 to the user. Wireless communication device 400 uses display 402 to output a visual alert 442 including the matching allergen(s) 444 and the approximate distance 446. Speaker 407 may output an aural alert while a vibrator outputs a tactile alert. Once the user acknowledges the alert, the user may activate keypad 404 to clear the alert or gain more information about the alert.

In other embodiments, alerts may come in many variations including any combination of outputs available on the wireless communication device. Some alerts may be simple while other alerts are complex.

Figure 5:
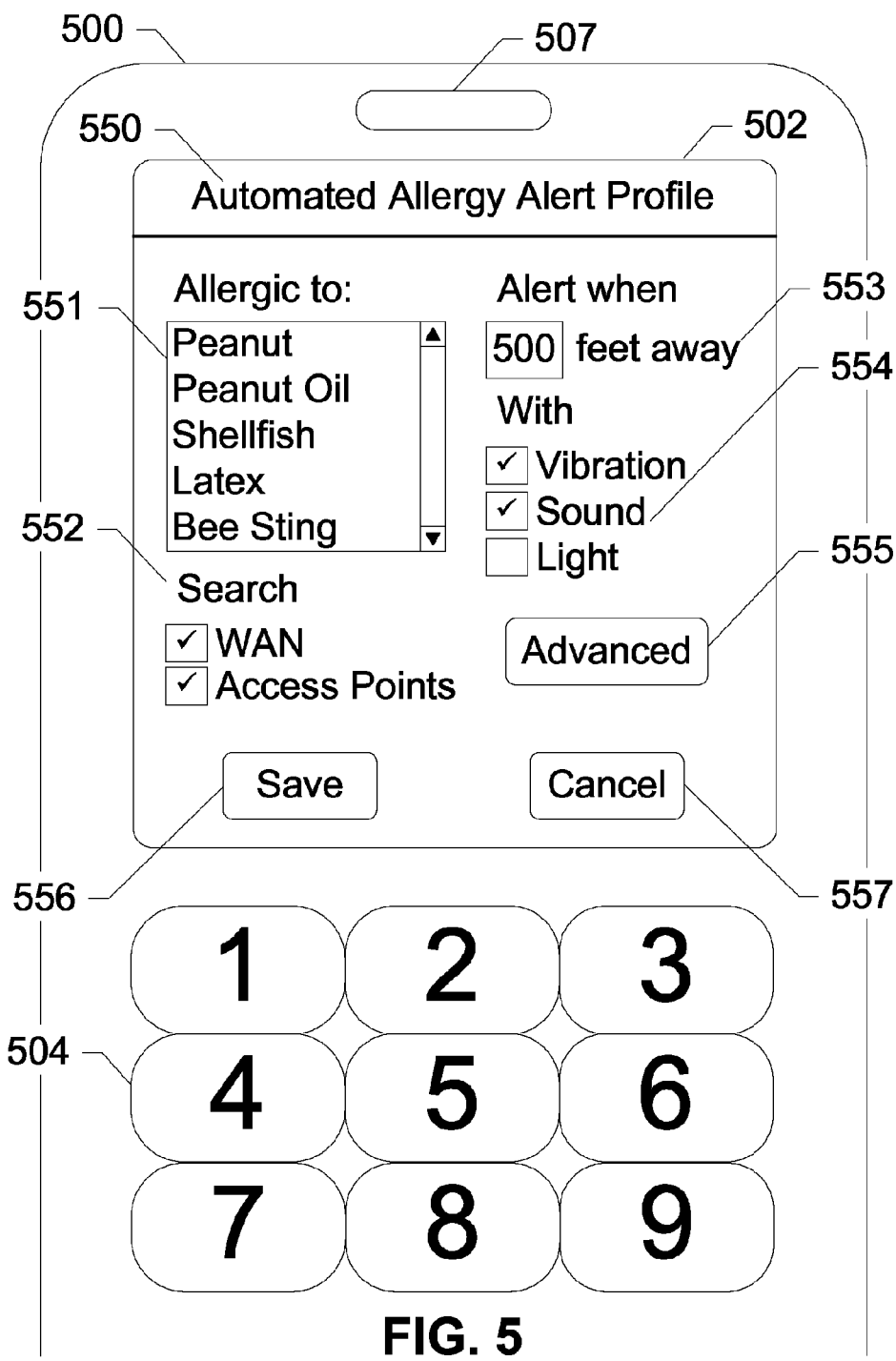
FIG. 5 shows a wireless communication device for editing an allergy profile, according to an exemplary embodiment of the present subject disclosure.

FIG. 5 shows a wireless communication device 500 for editing an allergy profile 550, according to an exemplary embodiment of the present subject disclosure. In this exemplary embodiment, allergy profile 550 includes a list of allergens 551 to which the user is currently allergic, a search location(s) 552, a radius of alert 553, an alert output 554, an advanced options button 555, a save button 556, and a cancel button 557. The user inputs selections using keypad 504. Allergens 551 are entered by the user or a trusted medical professional to ensure the list is correct, accurate, and current. Selection of search location 552 allows the user to choose whether to focus on a wide-area network (WAN), such as a cellular network, individual network nodes, such as restaurant WiFi signals, or both. Radius of alert 553 allows the user to specify a distance within which to be alerted of an allergen. Alert output 554 is included to allow the user to select a vibration from the vibrator, a sound from speaker 507, a light or otherwise visual output from display 502 or another light source such as a flash, or any combination including all three outputs. Advanced options button 555 is selected by the user to enter more specific options.

The allergy profile can be set up from other electronic devices other than the wireless communication device, such as a home computer, or any other device storing or in communication with the allergy profile. In most embodiments, the user must enter a password or pass a form of security and privacy safeguards before being able to edit the allergens to which they are allergic. In some embodiments, many more options can be added, giving the user greater flexibility and specifying more detailed instructions on how the allergy alert logic should perform. Users may be allergic to certain allergens to vastly different degrees. For example, a user may have a life-threatening allergy to peanuts, but only a slight, non life-threatening, allergy to shellfish. In this case, the user may want to specify different types of alerts depending on the allergen. When shellfish are found, a discreet alert may be executed, such as a vibration only. However, if peanuts are found, the alert may make use of any and all means to alert the user. Alerts may also change with the user's schedule. In these embodiments, the user can specify different alerts per the time of day, day of the week, etc. While the allergy alert logic is designed to keep information private, a user may want to allow allergy information to be accessible under special circumstances, such as for an EMT arriving to help an injured user. The radius of alert may not be an exact measure, but a calculated estimation erred on the safe side. This can be accomplished using GPS measurements, response time delay, and other methods known to those having ordinary skill in the art.

In exemplary embodiments where the wireless communication device accesses a central database for allergy information, the wireless communication device is capable of determining the location(s) of allergens for a much wider area than when the wireless communication device relies on short-range networks. With this capability, a user can plan a route and determine if and where allergens are present before making the route. Many other possibilities open up with the capability to determine allergen locations on a large scale.

Figure 6:
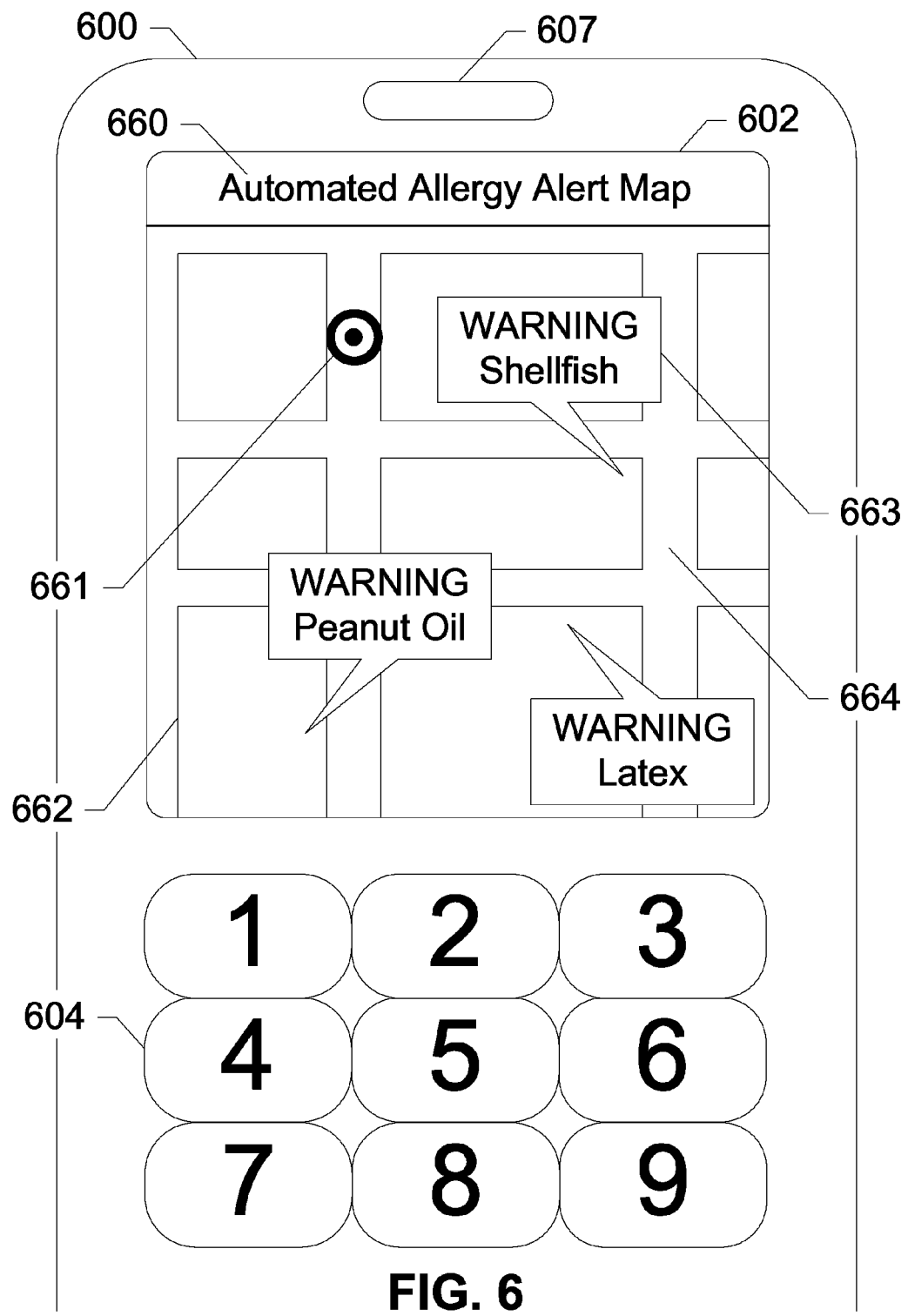
FIG. 6 shows an allergy alert map on a wireless communication device, according to an exemplary embodiment of the present subject disclosure.

FIG. 6 shows an allergy alert map 660 on a wireless communication device 600, according to an exemplary embodiment of the present subject disclosure. In this exemplary embodiment, allergy alert map 660 is output to display 602, and includes a user location 661, a plurality of buildings 662, an allergy alert 663, and a plurality of roads 664. Wireless communication device 600 has received allergy codes from an allergy server on a wide-area network. After receiving location information for wireless communication device 600, the server has sent allergy codes from a plurality of locations near the user. Allergy alerts 663 have been placed on allergy alert map 660 at the relative locations. Allergy alerts 663 include the allergen present at the location. Allergy alert map 660 shows user location 661 relative to any locations having allergens to which the user is allergic. Allergy alert map 660 is updated in real-time as the user moves and changes location. New alerts will appear as wireless communication device 600 receives new allergen information from an allergy announcement that matches the allergens in the user's allergy profile.

In some embodiments, the user location is constantly in the center of the display, while the rest of the map moves around the user location. The allergy alert map can zoom in or zoom out to the user's desire.

In certain scenarios it may be more efficient not to use an automated alert.

For food vending machines where the food rarely changes and there are no practical means for maintaining an updatable server-based allergy database, the appropriate mechanism would be to use NFC. In exemplary embodiments, an NFC tag contains the list of allergens that may be present in the packaged food displayed in the vending machine(s). In this case the user places an NFC-enabled wireless communication device near the tag so that the allergy alert logic can read the list of allergens from the tag. If a match is found, the allergy alert logic alerts the user. When the food is changed in the vending machine, the tag is updated, or a new tag replaces the old one. Since many NFC tags are inexpensive and disposable there is virtually no economic impact.

Figure 7:
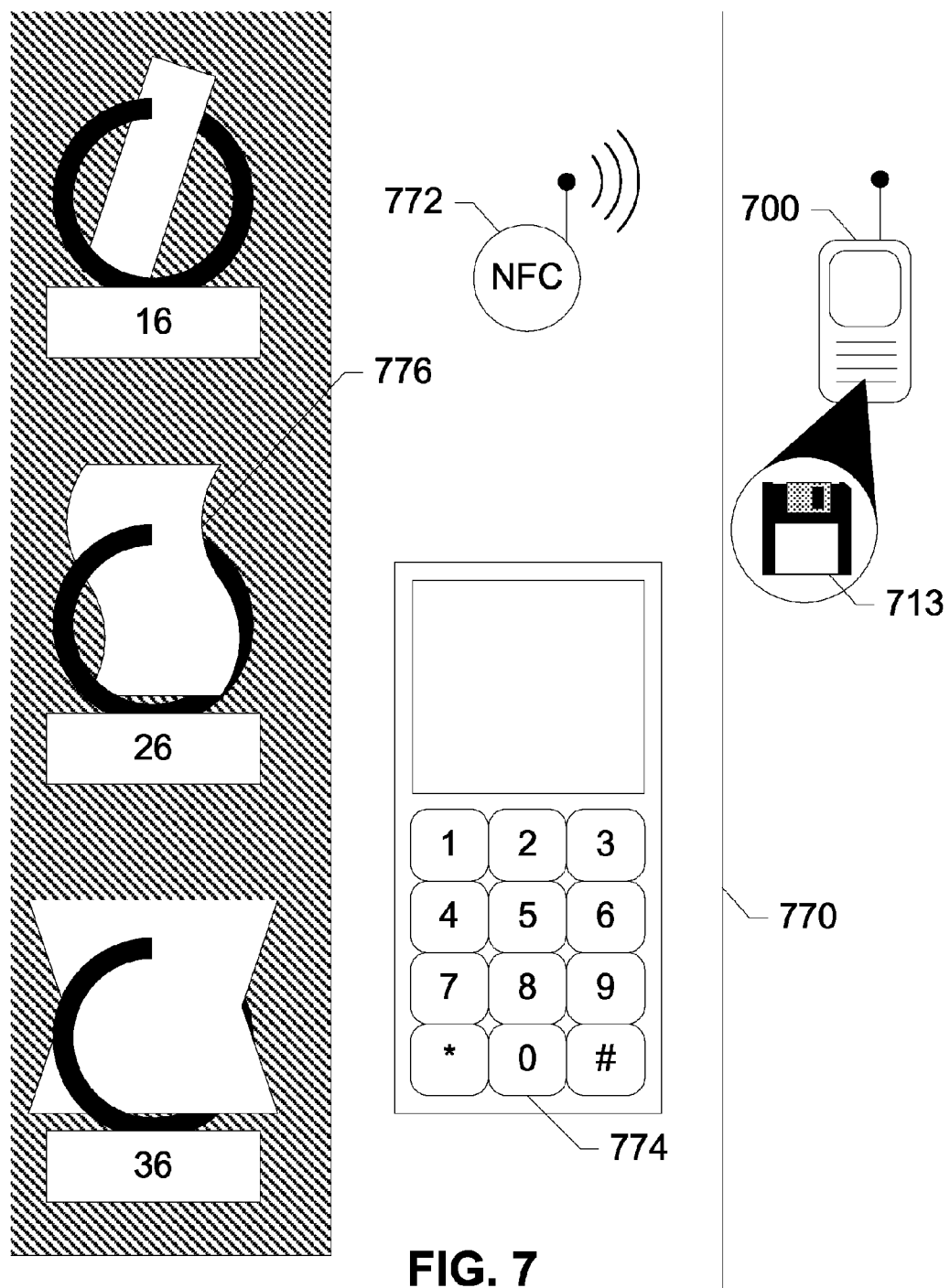
FIG. 7 shows a vending machine equipped for automated allergy alerts, according to an exemplary embodiment of the present subject disclosure.

FIG. 7 shows a vending machine 770 equipped for automated allergy alerts, according to an exemplary embodiment of the present subject disclosure. In this exemplary embodiment, vending machine 770 includes a passive NFC tag 772 containing the most recent update of allergen codes contained in the plurality of offered snacks 776, along with a keypad 774. A wireless communication device 700 including allergy alert logic 713 interacts with vending machine 770 to receive an allergy announcement by reading associated NFC tag 772 when wireless communication device 700 is within in the immediate proximity of 772. Wireless communication device 700 uses allergy alert logic 713 to compare allergy information with the user's allergy profile. This allergy information is specific to each snack 776. If any of the items contain allergens to which the user is allergic, allergy alert logic 713 outputs the snack and the allergens in the form of an alert on wireless communication device 700.

In similar vending machine embodiments, the wireless communication device is used to read the NFC tags on a vending machine to download the information other than food allergens. For example, the NFC tags may be used to communicate the percent of saturated fat, sodium concentration or levels of transfats. The non-allergen food information may be transmitted using a different coding scheme than that of allergens.

Many of the examples herein refer to common food-born allergens from restaurants, cafeterias, vending machines, etc., but the disclosure extends to other sources and handlers of food products, such as grocery stores, food banks, grocery delivery trucks, etc. Moreover, embodiments of the present subject disclosure are also used in alerts for other non-food allergens, such as chemical, biological, clinical, etc., from factories, foundries, plants, etc., that can activate an allergic reaction from a user. In further embodiments, parks and recreational facilities perform announcements to inform users of locations of bee and wasp hives, poison ivy, hazardous materials, etc. Health hazards such as the presence of cancer causing substances can be announced to wireless communication devices. Even non allergen food related information, such as daily value of sodium, cholesterol, saturated fat, etc., from a product vending machine, restaurant, etc., are useful to users and can be announced using the present subject disclosure. Virtually any location having any substances capable of having a negative medical impact can make use of this disclosure. Many other locations and uses will become apparent to those having skill in the art upon reading this disclosure.

The foregoing disclosure of the exemplary embodiments of the present subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure. The scope of the subject disclosure is to be defined only by the claims appended hereto, and by their equivalents.

Further, in describing representative embodiments of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequences may be varied and still remain within the spirit and scope of the present subject disclosure.

What is claimed is:

1. A wireless communication device, comprising:
a memory to store instructions; and
a processor coupled to the memory, wherein responsive to executing the instructions, the processor performs operations comprising:
receiving an allergy announcement from a server via a network, the announcement identifying an allergen present at a first location corresponding to a network node of a plurality of network nodes in communication with the server, the server being at a second location remote from the first location and from the wireless communication device,
determining that the allergen present at the first location is in an allergy profile of a user stored in the memory at the wireless communication device, wherein the allergy profile includes information regarding a sensitivity of the user to allergens;
determining an approximate distance of the wireless communication device from the first location responsive to receiving the allergy announcement, and
alerting the user of the first location and the allergen, in accordance with the allergy profile and the approximate distance,
wherein the allergen is included in an allergen database referenced by the server, and
wherein the allergen database includes updates received at the server via the network regarding allergens present at respective locations of the network nodes, the updates provided by personnel at each of the locations having first-hand knowledge of the allergens present at that location.

2. The device in claim 1, wherein the allergy announcement is received from a network node in communication with the server, and
wherein the network comprises one of a short-range local-area or a wide-area network.

3. The device in claim 2, wherein the server receives the updates from network nodes having locations within a designated coverage area.

4. The device in claim 3, wherein the database is updated as each allergen is introduced at each of the respective locations of the network nodes.

5. The device in claim 1, wherein the operations further comprise activating activates one of a display, a speaker, or a vibrator responsive to the alerting the user of the first location and the allergen.

6. The device in claim 1, wherein the allergy announcement is for a plurality of locations, and
wherein the operations further comprise:
requesting the allergy announcement from the server;
displaying a map on a display in communication with the processor; and
indicating a location of the allergen on the map.

7. The device in claim 1, wherein the allergy profile includes medical information associated with the sensitivity of the user to allergens.

8. The device in claim 1, wherein the first location comprises one of a restaurant, a store, a factory, a food handling facility, or a vending machine.

9. A system for allergy alerts, the system comprising:
a server comprising a processor in communication with a wireless communication device via a network, the server being in communication with a plurality of network nodes;
a memory to store instructions; and
a processor coupled to the memory and the server, wherein responsive to executing the instructions, the processor performs operations comprising:
receiving from the server an allergy announcement, the announcement including allergens present at a first location corresponding to a network node of the plurality of network nodes, the server being at a second location remote from the first location and from the wireless communication device,
determining that an allergen present at the first location is in an allergy profile of a user stored in a memory at the wireless communication device, wherein the allergy profile includes information regarding a sensitivity of the user to allergens; and
alerting the user of the first location and the allergen; and
an allergen database in communication with the server and with each of the plurality of network nodes, the allergen database including allergens present at respective locations of the network nodes,
wherein the allergen database includes updates received at the server via the network regarding the allergens present at the respective locations, the updates provided by personnel at each of the locations having first-hand knowledge of allergens present at that location, and
wherein an alert by the wireless communication device is in accordance with the allergy profile and an approximate distance of the wireless communication device from the first location responsive to receiving the allergy announcement, the allergy profile including a sensitivity of the user to the allergen.

10. The system in claim 9, wherein the allergy announcement is received from a network node in communication with the server and operating on one of a short-range communication protocol and a wide-area communication protocol.

11. The system in claim 10, wherein the network node operates on Near Field Communication (NFC), a Local Area Network, or a Wide Area Network WAN.

12. The system in claim 9, wherein the operations further comprise requesting the allergy announcement from the server, and wherein the request includes the first location.

13. The system in claim 9, wherein the allergen database includes updates received from network nodes having locations within a designated coverage area.

14. The system in claim 9, wherein the allergen database is updated as each allergen is introduced at each of the respective locations of the network nodes.

15. The device in claim 9, wherein the location a restaurant, a store, a factory, or a vending machine.

16. A method for alerting a user of a first location having an allergen, the method comprising:
receiving, by a wireless communication device of the user, an allergy announcement sent from a server via a network, the announcement including an allergen present at the first location, the server being at a second location remote from the first location and from the wireless communication device,
wherein the allergen is included in an allergen database referenced by the server,
wherein the allergen database includes updates received at the server via the network from a plurality of network nodes of the network regarding allergens present at respective locations of the network nodes, the updates provided by personnel at each of the locations having first-hand knowledge of allergens present at that location;

determining, by the wireless communication device, that the allergen included in the announcement and present at the first location is in an allergy profile stored in a memory at the wireless communication device, wherein the allergy profile includes information regarding a sensitivity of the user to allergens;

determining, by the wireless communication device, an approximate distance of the wireless communication device from the first location responsive to receiving the allergy announcement; and alerting, by the wireless communication device, the user of the first location and the allergen, wherein an alert by the wireless communication device is in accordance with the allergy profile and the approximate distance, the allergy profile including a sensitivity of the user to the allergen.

17. The method in claim 16, wherein the alerting includes activating a display, a speaker, or a vibrator of the wireless communication device.

18. The method in claim 16, further comprising requesting the allergy announcement from the server, the request including the first location.

19. The method in claim 16, further comprising receiving from a network node corresponding to the first location a list of items present at the first location which contain allergens in the allergy profile.

20. The method in claim 16, wherein the alerting includes displaying the first location on a map, wherein the map is output to a display on the wireless communication device.

* * * * *